(12) United States Patent
Tsugawa et al.

(10) Patent No.: US 11,024,663 B2
(45) Date of Patent: Jun. 1, 2021

(54) SOLID-STATE IMAGING ELEMENT, ELECTRONIC APPARATUS, AND SEMICONDUCTOR DEVICE

(71) Applicant: SONY SEMICONDUCTOR SOLUTIONS CORPORATION, Kanagawa (JP)

(72) Inventors: Hidenobu Tsugawa, Kanagawa (JP); Tomoharu Ogita, Kanagawa (JP)

(73) Assignee: SONY SEMICONDUCTOR SOLUTIONS CORPORATION, Kanagawa (JP)

(*) Notice: Subject to any disclaimer, the term of this patent is extended or adjusted under 35 U.S.C. 154(b) by 0 days.

(21) Appl. No.: 16/496,752

(22) PCT Filed: Mar. 16, 2018

(86) PCT No.: PCT/JP2018/010378
§ 371 (c)(1),
(2) Date: Sep. 23, 2019

(87) PCT Pub. No.: WO2018/180570
PCT Pub. Date: Oct. 4, 2018

(65) Prior Publication Data
US 2020/0035735 A1 Jan. 30, 2020

(30) Foreign Application Priority Data
Mar. 30, 2017 (JP) .............................. JP2017-067655

(51) Int. Cl.
*H01L 27/146* (2006.01)
*A61B 1/05* (2006.01)
(Continued)

(52) U.S. Cl.
CPC ........ *H01L 27/14634* (2013.01); *A61B 1/051* (2013.01); *H01L 27/14636* (2013.01);
(Continued)

(58) Field of Classification Search
CPC ......... H01L 27/14634; H01L 27/14636; A61B 1/051; H04N 5/379; B60R 11/04; B60R 16/0231; G05D 1/021
(Continued)

(56) References Cited

U.S. PATENT DOCUMENTS

| 9,391,111 | B1* | 7/2016 | Mabuchi ........... H01L 27/14609 |
| 2007/0029636 | A1* | 2/2007 | Kanemaru ............. H01L 27/12 257/510 |
| 2015/0270307 | A1 | 9/2015 | Umebayashi et al. | |

FOREIGN PATENT DOCUMENTS

| JP | 2006/332478 A | 12/2006 |
| JP | 2014-099582 A | 5/2014 |
| WO | 2014/061240 A1 | 4/2014 |

OTHER PUBLICATIONS

International Search Report and Written Opinion of PCT Application No. PCT/JP2018/010378, dated May 29, 2018, 08 pages of ISRWO.

* cited by examiner

*Primary Examiner* — Tong-Ho Kim
(74) *Attorney, Agent, or Firm* — Chip Law Group

(57) ABSTRACT

The present technology relates a solid-state imaging element, an electronic apparatus, and a semiconductor device each of which enables deterioration of electrical characteristics in a well region of a semiconductor element formed in a thinned semiconductor substrate to be restrained. A solid-state imaging element as a first aspect of the present technology is a solid-state imaging element constituted by laminating semiconductor substrates in three or more layers, in which of the laminated semiconductor substrates, at least one sheet of the semiconductor substrate is thinned, and an impurity region whose carrier type is the same as that of the thinned semiconductor substrate is formed between a well (Continued)

region and a thinned surface portion in the thinned semiconductor substrate. The present technology can, for example, be applied to a CMOS image sensor.

7 Claims, 11 Drawing Sheets

(51) Int. Cl.
 *H04N 5/369* (2011.01)
 *B60R 11/04* (2006.01)
 *B60R 16/023* (2006.01)
 *G05D 1/02* (2020.01)
(52) U.S. Cl.
 CPC ........... *B60R 11/04* (2013.01); *B60R 16/0231* (2013.01); *G05D 1/021* (2013.01); *H04N 5/379* (2018.08)
(58) Field of Classification Search
 USPC ........................................................ 257/444
 See application file for complete search history.

SOLID-STATE IMAGING ELEMENT, ELECTRONIC APPARATUS, AND SEMICONDUCTOR DEVICE

CROSS REFERENCE TO RELATED APPLICATIONS

This application is a U.S. National Phase of International Patent Application No. PCT/JP2018/010378 filed on Mar. 16, 2018, which claims priority benefit of Japanese Patent Application No. JP 2017-067655 filed in the Japan Patent Office on Mar. 30, 2017. Each of the above-referenced applications is hereby incorporated herein by reference in its entirety.

TECHNICAL FIELD

The present technology relates to a solid-state imaging element, an electronic apparatus, and a semiconductor device, and more particularly to a solid-state imaging element, an electronic apparatus, and a semiconductor device each of which is suitable for being used in a case where a semiconductor substrate is thinned and laminated.

BACKGROUND ART

Heretofore, in a device using a semiconductor substrate (hereinafter, also referred to as a semiconductor device), for the purpose of restraining an increase in chip area, wiring resistance, power consumption and the like, a structure in which a plurality of semiconductor substrates is laminated has been proposed (e.g., refer to PTL 1).

A method in which after firstly, in a wafer process, a plurality of semiconductor substrates is laminated and electrically connected, the resulting lamination body is divided into individual pieces each having a chip size is known as a method of laminating a plurality of semiconductor substrates. Practically, a CMOS image sensor including a logic substrate and a sensor substrate is manufactured by using the method described above, and a CMOS image sensor in which three or more sheets of semiconductor substrates are laminated, or other semiconductor devices also exist.

Incidentally, in the case where a plurality of semiconductor substrates is laminated to form a semiconductor device, in order to thin a total thickness, and make a through-via to be provided between laminated semiconductor substrates easy to open, the semiconductor substrates other than a lower layer substrate (which needs to have a thickness for holding strength of the whole device) needs to be thinned.

CITATION LIST

Patent Literature

[PTL 1]
JP 2009-88430A

SUMMARY

Technical Problem

However, in the case where a semiconductor substrate is thinned, a well region of a semiconductor element formed in the semiconductor substrate is depleted. When the depletion layer reaches a thinned interface portion, the electrical characteristics of the well region are deteriorated. Specifically, a leakage current caused to flow via defect levels and reduction in inter-well withstand voltage are caused.

The present technology has been made in the light of such a situation, and enables deterioration of electrical characteristics in a well region of a semiconductor element formed in a thinned semiconductor substrate to be restrained.

Solution to Problem

A solid-state imaging element of a first aspect of the present disclosure is a solid-state imaging element constituted by laminating semiconductor substrates in three or more layers, in which of the laminated semiconductor substrates, at least one sheet of the semiconductor substrate is thinned, and an impurity region whose carrier type is the same as that of the thinned semiconductor substrate is formed between a well region and a thinned surface portion in the thinned semiconductor substrate.

An impurity region whose carrier type is the same as that of the thinned semiconductor substrate can be caused to be formed between a well region whose carrier type is different from that of the thinned semiconductor substrate, and the thinned surface portion in the thinned semiconductor substrate.

An impurity region whose carrier type is the same as that of the thinned semiconductor substrate can be caused to be formed between the well region whose carrier type is different from that of the thinned semiconductor substrate and a well region whose carrier type is the same as that of the thinned semiconductor substrate, and the thinned surface portion in the thinned semiconductor substrate.

A layer including an impurity region whose carrier type is the same as that of the thinned semiconductor substrate can be caused to be formed over an entire surface between the well region and the thinned surface portion in the thinned semiconductor substrate.

The impurity region whose carrier type is the same as that of the semiconductor substrate can be caused to be formed only between the well region whose carrier type is different from that of the thinned semiconductor substrate and the thinned surface portion in the thinned semiconductor substrate.

In a case where the thinned semiconductor substrate including a P-type substrate, a P-type impurity region can be caused to be formed between an Nwell region and the thinned surface portion of the semiconductor substrate.

In a case where the thinned semiconductor substrate including an N-type substrate, an N-type impurity region can be caused to be formed between a Pwell region and the thinned surface portion of the semiconductor substrate.

An impurity region whose carrier type is the same as that of the thinned semiconductor substrate can be caused to be formed at concentration such that it may be impossible for a depletion layer capable of extending from a well region to reach an interface of the thinned semiconductor substrate between the well region and the thinned surface portion in the thinned semiconductor substrate.

A through-via can be caused to be formed in the thinned semiconductor substrate.

An electronic apparatus as a second aspect of the present technology is an electronic apparatus equipped with a solid-state imaging element constituted by laminating semiconductor substrates in three or more layers, in which in the solid-state imaging element, of the laminated semiconductor substrates, at least one sheet of the semiconductor substrate is thinned, and an impurity region whose carrier type is the same as that of the thinned semiconductor substrate is formed between a well region and a thinned surface portion in the thinned semiconductor substrate.

A semiconductor device as a third aspect of the present technology is a semiconductor device constituted by laminating semiconductor substrates in three or more layers, in which of the laminated semiconductor substrates, at least one sheet of the semiconductor substrate is thinned, and an impurity region whose carrier type is the same as that of the thinned semiconductor substrate is formed between a well region and a thinned surface portion in the thinned semiconductor substrate.

Advantageous Effect of Invention

According to the first to third aspects of the present technology, it is possible to restrain the deterioration of the electrical characteristics in the well region of the semiconductor element formed in the thinned semiconductor substrate.

DESCRIPTION OF EMBODIMENTS

Hereinafter, the best modes for carrying out the present technology (hereinafter, referred to as embodiments) will be described with reference to the drawings.

1. First Embodiment

Figure 1:
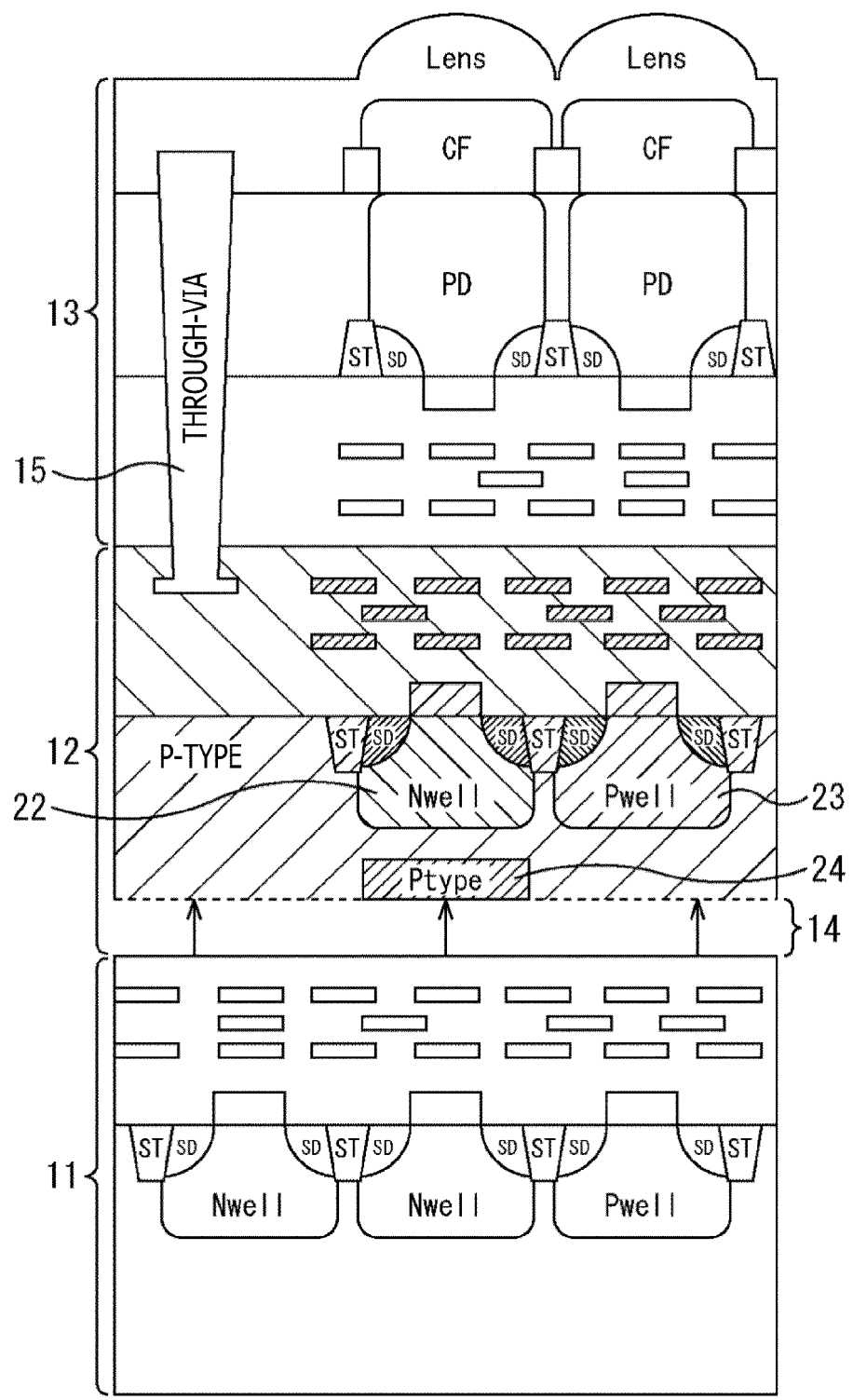
FIG. 1 is a cross-sectional view depicting an example of a structure of a solid-state imaging element as a first embodiment of the present technology.

FIG. 1 is a cross-sectional view depicting an example of a structure of a solid-state imaging element as a first embodiment of the present technology. The first embodiment is constituted by laminating three sheets of semiconductor substrates, i.e., a lower layer substrate 11, an intermediate substrate 12, and an upper layer substrate 13.

The lower layer substrate 11 is a substrate in which a logic circuit in the solid-state imaging element is formed. It should be noted that since the lower layer substrate 11 has role of holding the strength of the solid-state imaging element, the lower layer substrate 11 is not basically thinned. However, the lower layer substrate 11 may be thinned within the range where the strength of the solid-state imaging element is maintained.

The intermediate substrate 12 is a substrate in which the logic circuit in the solid-state imaging element is formed, and is made a target of the thinning.

The upper layer substrate 13 is a substrate in which a sensor circuit in the solid-state imaging element is formed. A through-via 15 is formed between the intermediate substrate 12 and the upper layer substrate 13, and the intermediate substrate 12 and the upper layer substrate 13 are electrically connected to each other via an electrode formed in the through-via 15.

An Nwell region 22 and a Pwell region 23 are formed as constituent elements of the semiconductor elements in the intermediate substrate 12.

Further, a region into which the impurities of the same carrier type as that of the intermediate substrate 12 is formed between at least the well region, whose carrier type (P-type or N-type) is different from that of the intermediate substrate 12, of the Nwell region 22 and the Pwell region 23, and a thinned back surface portion (a lower side surface portion in the figure) of the intermediate substrate 12 is formed in the intermediate substrate 12.

In case of the first embodiment, the intermediate substrate 12 is composed of a P-type substrate 21. Therefore, a P-type region 24 filled with holes is formed between at least the Nwell region 22 of the Nwell region 22 and the Pwell region 23, and the back surface portion to be thinned of the intermediate substrate 12. It should be noted that the P-type region 24 has concentration such that a depletion layer extending from the Nwell region 22 does not reach an interface of the intermediate substrate 12.

After the P-type region 24 is formed between the Nwell region 22 and the back surface portion of the intermediate substrate 12, a cut region 14 is cut from a direction indicated by arrows in the figure to thin the intermediate substrate 12. Thereafter, the intermediate substrate 12 is laminated on the lower layer substrate 11.

Even when since the P-type region 24 is formed, the intermediate substrate 12 is thinned from the back surface side, the depletion layer which can extend from the Nwell region 22 does not reach the interface of the intermediate substrate 12. Therefore, it is possible to restrain the generation of the leakage current caused to flow via the defect levels, and the reduction of the inter-Well withstand voltage.

2. Second Embodiment

Figure 2:
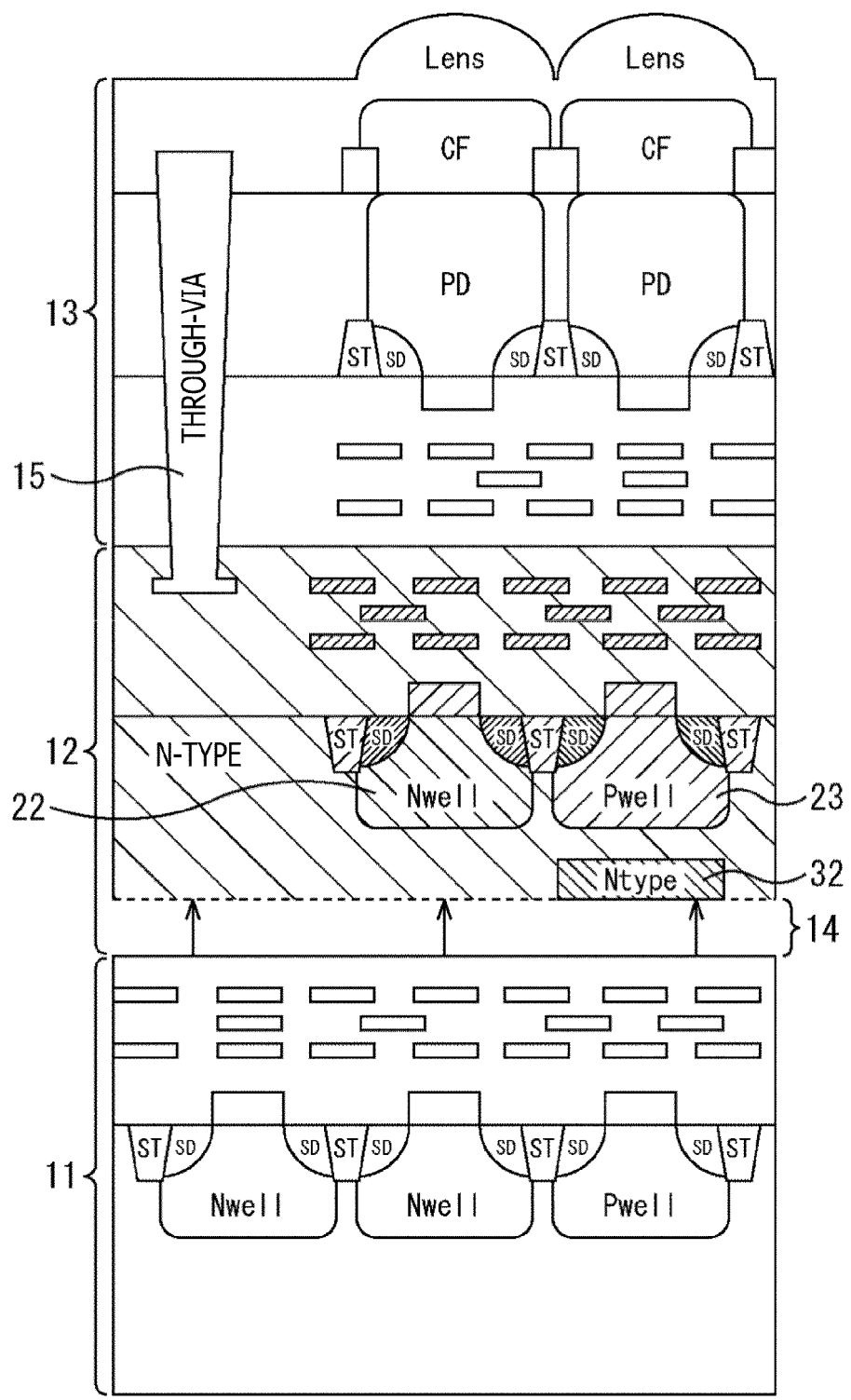
FIG. 2 is a cross-sectional view depicting an example of a structure of a solid-state imaging element as a second embodiment of the present technology.

FIG. 2 is a cross-sectional view depicting an example of a structure of a solid-state imaging element as a second embodiment of the present technology. In the second embodiment, the carrier type of the intermediate substrate 12 is different from that in case of the first embodiment. It should be noted that since the constituent elements common to those of the first embodiment are respectively denoted by the same reference signs, a description thereof is suitably omitted. This also applies to other embodiments described below.

In the second embodiment, the intermediate substrate 12 as the target of the thinning is composed of an N-type substrate 31. Therefore, an N-type region 32 filled with electrons is formed between at least the Pwell region 23 of the Nwell region 22 and the Pwell region 23, and the back surface portion to be thinned of the intermediate substrate 12. It should be noted that the N-type region 32 has concentration such that a depletion layer extending from the Pwell region 23 does not reach an interface of the intermediate substrate 12.

After the N-type region 32 is formed between the Pwell region 23 and the intermediate substrate 12, the cut region 14 is cut from the direction indicated by the arrows in the figure to thin the intermediate substrate 12. Thereafter, the intermediate substrate 12 is laminated on the lower layer substrate 11.

Even when since the N-type region 32 is formed, the intermediate substrate 12 is thinned from the back surface side, the depletion layer which can extend from the Pwell region 23 does not reach the interface of the intermediate substrate 12. Therefore, it is possible to restrain the generation of the leakage current caused to flow via the defect levels, and the reduction of the inter-Well withstand voltage.

3. Third Embodiment

Figure 3:
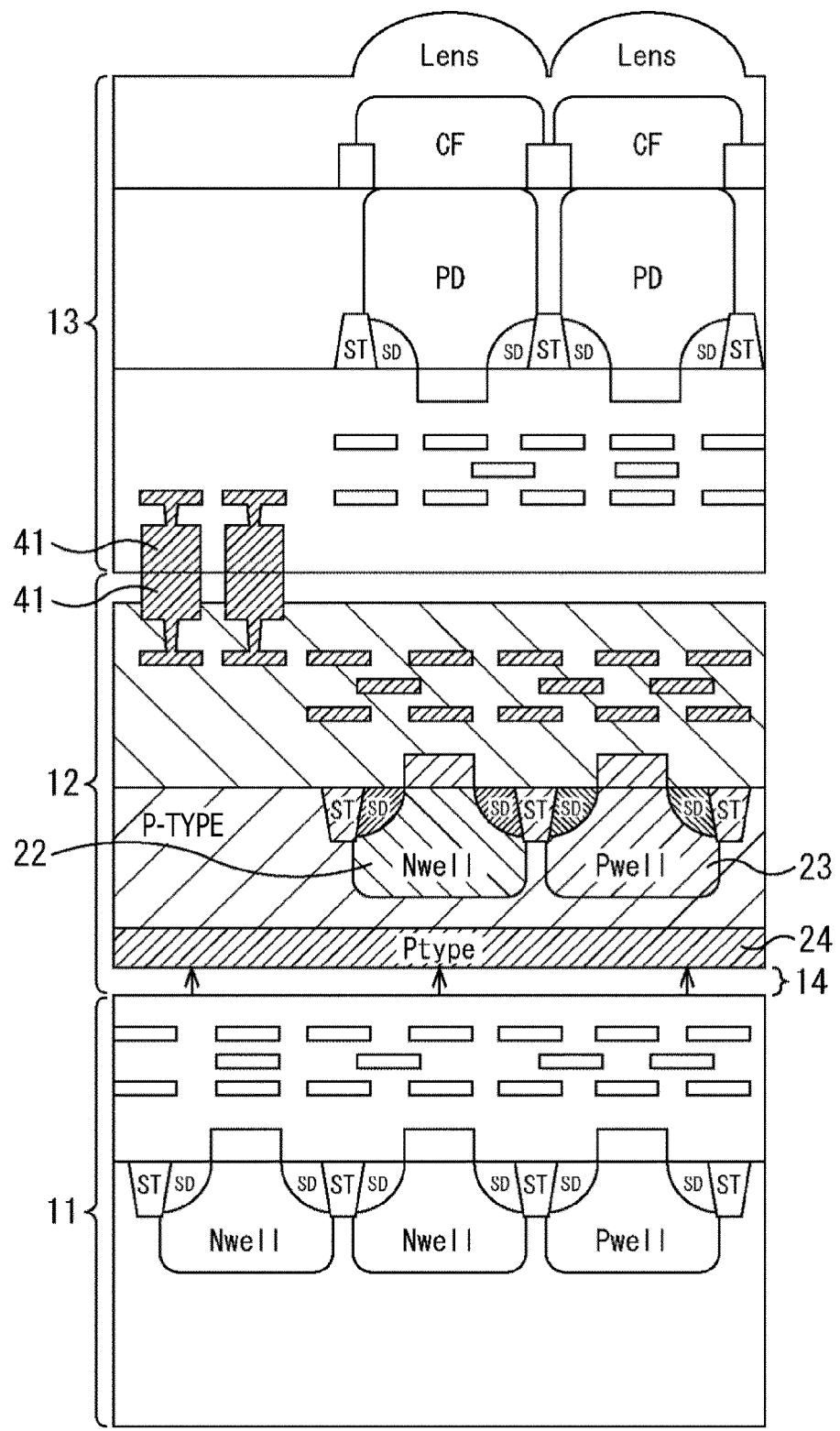
FIG. 3 is a cross-sectional view depicting an example of a structure of a solid-state imaging element as a third embodiment of the present technology.

FIG. 3 is a cross-sectional view depicting an example of a structure of a solid-state imaging element as a third embodiment of the present technology. The third embodiment is constituted by laminating three sheets of semiconductor substrates, i.e., the lower layer substrate 11, the intermediate substrate 12, and the upper layer substrate 13.

The lower layer substrate 11 is a substrate in which a logic circuit in the solid-state imaging element is formed. It should be noted that since the lower layer substrate 11 has the role of holding the strength of the solid-state imaging element, the lower layer substrate 11 is not basically thinned. However, the lower layer substrate 11 may be thinned within the range where the strength of the solid-state imaging element is maintained.

The intermediate substrate 12 is a substrate in which the logic circuit in the solid-state imaging element is formed, and is made a target of the thinning.

The upper layer substrate 13 is a substrate in which a sensor circuit in the solid-state imaging element is formed. A connection pad 41 made of a metal material such as Cu is formed in each of the intermediate substrate 12 and the upper layer substrate 13 which is laminated on the intermediate substrate 12. The intermediate substrate 12 and the upper layer substrate 13 are electrically connected to each other via the two connection pads 41.

The Nwell region 22 and the Pwell region 23 are formed as the constituent elements of the semiconductor element in the intermediate substrate 12.

Further, in the intermediate substrate 12, a region into which the impurities of the same carrier type as that of the intermediate substrate 12 are introduced is formed over the whole intermediate substrate 12 between the well region, whose carrier type is different from that of the intermediate substrate 12, of the Nwell region 22 and the Pwell region 23, and the back surface portion of the intermediate substrate 12.

In case of the third embodiment, the intermediate substrate 12 is composed of a P-type substrate 21. Therefore, a P-type region 24 filled with the holes is formed over the whole intermediate substrate 12 between the Nwell region 22 and the back surface portion of the intermediate substrate 12. It should be noted that the P-type region 24 has concentration such that a depletion layer extending from the Nwell region 22 does not reach an interface of the intermediate substrate 12.

After the P-type region 24 is formed between the Nwell region 22 and the back surface portion of the intermediate substrate 12, a cut region 14 is cut from a direction indicated by arrows in the figure to thin the intermediate substrate 12. Thereafter, the intermediate substrate 12 is laminated on the lower layer substrate 11.

Even when since the P-type region 24 is formed, the intermediate substrate 12 is thinned from the back surface side, the depletion layer which can extend from the Nwell region 22 does not reach the interface of the intermediate substrate 12. Therefore, it is possible to restrain the generation of the leakage current caused to flow via the defect levels, and the reduction of the inter-Well withstand voltage.

4. Fourth Embodiment

Figure 4:
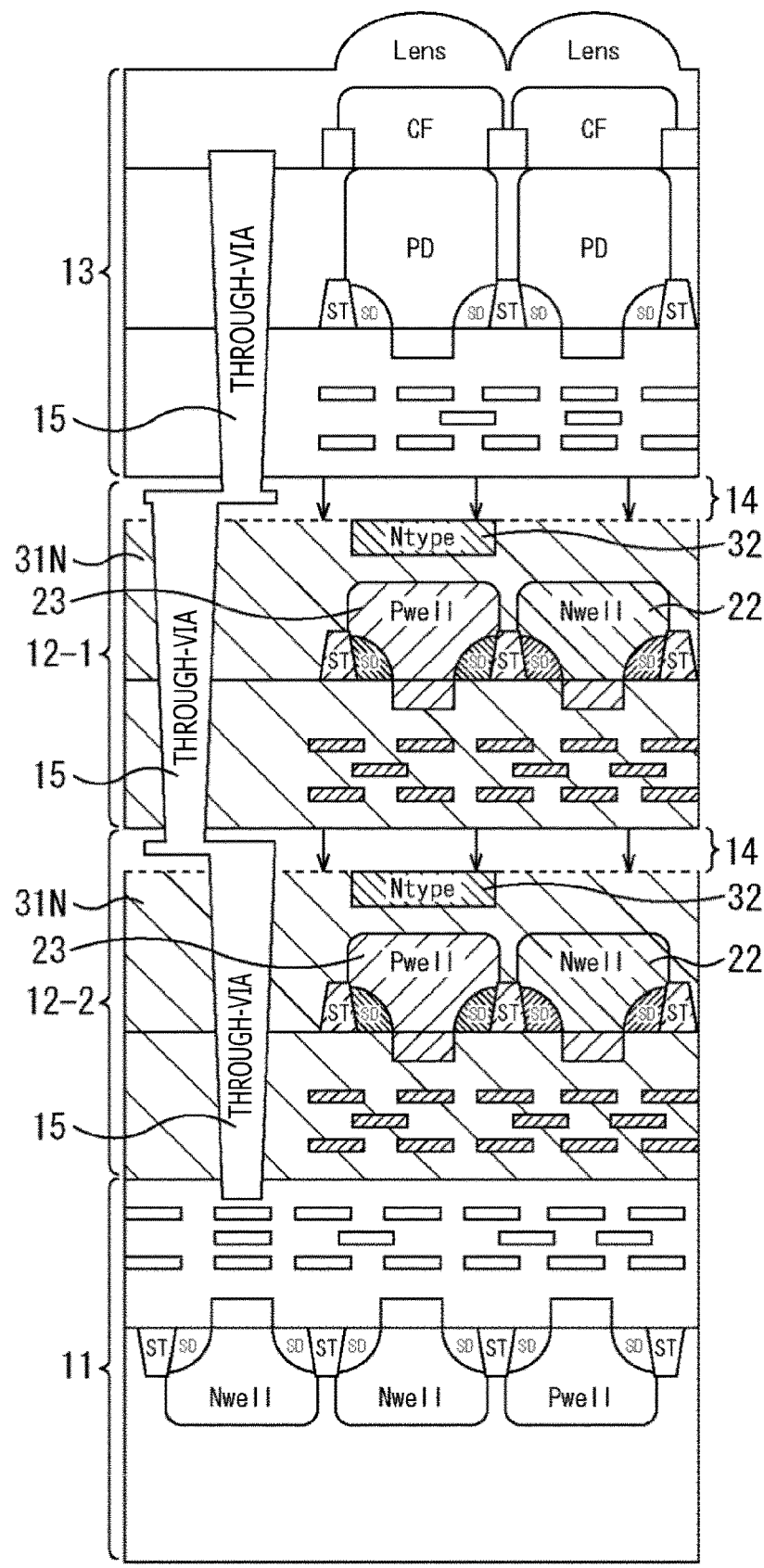
FIG. 4 is a cross-sectional view depicting an example of a structure of a solid-state imaging element as a fourth embodiment of the present technology.

FIG. 4 is a cross-sectional view depicting an example of a structure of a solid-state imaging element as a fourth embodiment of the present technology. The fourth embodiment is constituted by laminating the four sheets of semiconductor substrates, i.e., the lower layer substrate 11, intermediate substrates 12-1 and 12-2, and the upper layer substrate 13.

The lower layer substrate 11 is a substrate in which a logic circuit in the solid-state imaging element is formed. It should be noted that since the lower layer substrate 11 has role of holding the strength of the solid-state imaging element, the lower layer substrate 11 is not basically thinned. However, the lower layer substrate 11 may be thinned within the range where the strength of the solid-state imaging element is maintained.

The intermediate substrates 12-1 and 12-2 are substrates in which a logic circuit in the solid-state imaging element is formed, and are made the target of the thinning. Hereinafter, in the case where the intermediate substrates 12-1 and 12-2 need not to be individually distinguished from each other, the intermediate substrates 12-1 and 12-2 are simply referred to as the intermediate substrate 12.

The upper layer substrate 13 is a substrate in which a sensor circuit in the solid-state imaging element is formed.

The Nwell region 22 and the Pwell region 23 as the constituent elements of the semiconductor element are formed in the intermediate substrate 12 as the target of the thinning.

Further, a region into which the impurities of the same carrier type as that of the intermediate substrate 12 is formed between at least the well region, whose carrier type is different from that of the intermediate substrate 12, of the Nwell region 22 and the Pwell region 23, and a back surface portion to be thinned (an upper side surface portion in the figure) of the intermediate substrate 12 is formed in the intermediate substrate 12.

In case of the fourth embodiment, the intermediate substrate 12 is composed of a P-type substrate 31. Therefore, an N-type region 32 filled with the electrons is formed between at least the Pwell region 23 of the Nwell region 22 and the Pwell region 23, and the back surface portion of the intermediate substrate 12 (the upper side surface portion in the figure). It should be noted that the N-type region 32 has concentration such that the depletion layer extending from the Pwell region 23 does not reach an interface of the intermediate substrate 12.

After the N-type region 32 is formed between the Pwell region 23 and the back surface portion of the intermediate substrate 12, the cut region 14 is cut from the direction indicated by the arrows in the figure to thin the intermediate substrate 12-1. Thereafter, the intermediate substrate 12-1 is laminated on the lower layer substrate 11.

On the other hand, after the N-type region 32 is formed between the Pwell region 23 and the back surface portion of the intermediate substrate 12, the cut region 14 is cut from the direction indicated by the arrows in the figure to thin the intermediate substrate 12-2. Thereafter, the intermediate substrate 12-2 is laminated on the upper layer substrate 13.

Even when since the N-type region 32 is formed in the intermediate substrate 12, the intermediate substrate 12 is thinned from the back surface side, the depletion layer which can extend from the Pwell region 23 does not reach the interface of the intermediate substrate 12. Consequently, it is possible to restrain the generation of the leakage current caused to flow via the defect levels, and the reduction of the inter-Well withstand voltage.

Further, although in the fourth embodiment, the through-via 15 is formed in the intermediate substrate 12, since the intermediate substrate 12 is thinned, the through-via 15 can be formed without using a dedicated apparatus for forming the through-via 15 in a thick substrate. In addition, a machining time necessary for forming the through-via 15 can be shortened. Further, a diameter of the formed through-via can be made small, and thus the chip area can be reduced.

It is to be noted that although in case of the fourth embodiment, a method of cutting the two sheets of intermediate substrates 12 to be thinned is unified from the upper side in the figure, the intermediate substrates 12 which are cut from a lower side in the figure may be laminated. In addition, the intermediate substrate 12 cut from the upper side in the figure and the intermediate substrate 12 cut from the lower side in the figure may be mixed and laminated to constitute the solid-state imaging element.

5. Fifth Embodiment

Figure 5:
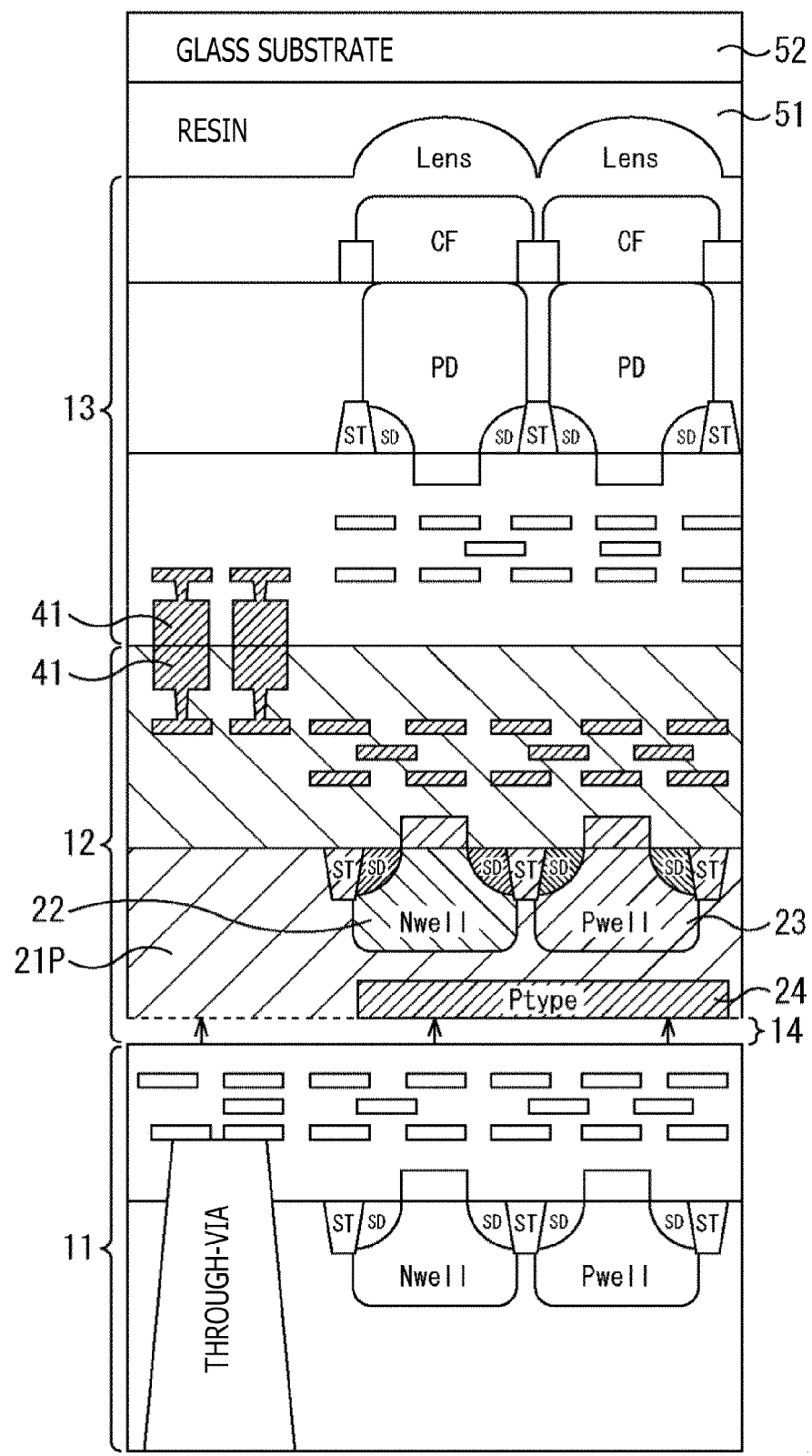
FIG. 5 is a cross-sectional view depicting an example of a structure of a solid-state imaging element as a fifth embodiment of the present technology.

FIG. 5 is a cross-sectional view depicting an example of a structure of a solid-state imaging element as a fifth embodiment of the present technology. The fifth embodiment is constituted by laminating the three sheets of semiconductor substrates, i.e., the lower layer substrate 11, the intermediate substrate 12, and the upper layer substrate 13.

The lower layer substrate 11 is a substrate in which the logic circuit in the solid-state imaging element is formed. It should be noted that since the lower layer substrate 11 has the role of holding the strength of the solid-state imaging element, the lower layer substrate 11 is not basically thinned. However, the lower layer substrate 11 may be thinned within the range where the strength of the solid-state imaging element is maintained.

The intermediate substrate 12 is a substrate in which the logic circuit of the solid-state imaging element is formed, and is made a target of the thinning.

The upper layer substrate 13 is a substrate equipped with a sensor circuit in the solid-state imaging element formed as WLCSP (Wafer level Chip Size Package). A resin 51 is filled in an upper surface of the upper layer substrate 13 and sealed with the glass 52. A connection pad 41 made of a metal material such as Cu is formed in each of the intermediate substrate 12 and the upper layer substrate 13 which is laminated on the intermediate substrate 12. The intermediate substrate 12 and the upper layer substrate 13 are electrically connected to each other via the two connection pads 41.

The Nwell region 22 and the Pwell region 23 are formed as the constituent elements of the semiconductor element in the intermediate substrate 12 as the target of the thinning.

Further, in the intermediate substrate 12, the region into which the impurities whose carrier type is the same as that of the intermediate substrate 12 is formed between at least the well region, whose carrier type is different from that of the intermediate substrate 12, of the Nwell region 22 and the Pwell region 23, and the back surface portion to be thinned (the lower side surface portion in the figure) of the intermediate substrate 12.

In case of the fifth embodiment, the intermediate substrate 12 is composed of a P-type substrate 21. Therefore, a P-type region 24 filled with the holes is formed between the Nwell region 22 and the Pwell region 23, and the back surface portion (the lower side surface portion in the figure) of the intermediate substrate 12. It should be noted that the P-type region 24 has concentration such that a depletion layer extending from the Nwell region 22 does not reach an interface of the intermediate substrate 12.

After the P-type region 24 is formed between the Nwell region 22 and the Pwell region 23, and the back surface portion of the intermediate substrate 12, a cut region 14 is cut from a direction indicated by arrows in the figure to thin the intermediate substrate 12. Thereafter, the intermediate substrate 12 is laminated on the lower layer substrate 11.

Even when since the P-type region 24 is formed, the intermediate substrate 12 is thinned from the back surface side, the depletion layer which can extend from the Nwell region 22 does not reach the interface of the intermediate substrate 12. Therefore, it is possible to restrain the generation of the leakage current caused to flow via the defect levels, and the reduction of the inter-Well withstand voltage.

6. With Respect to Thinning Amount of Intermediate Substrate 12

Figure 6:
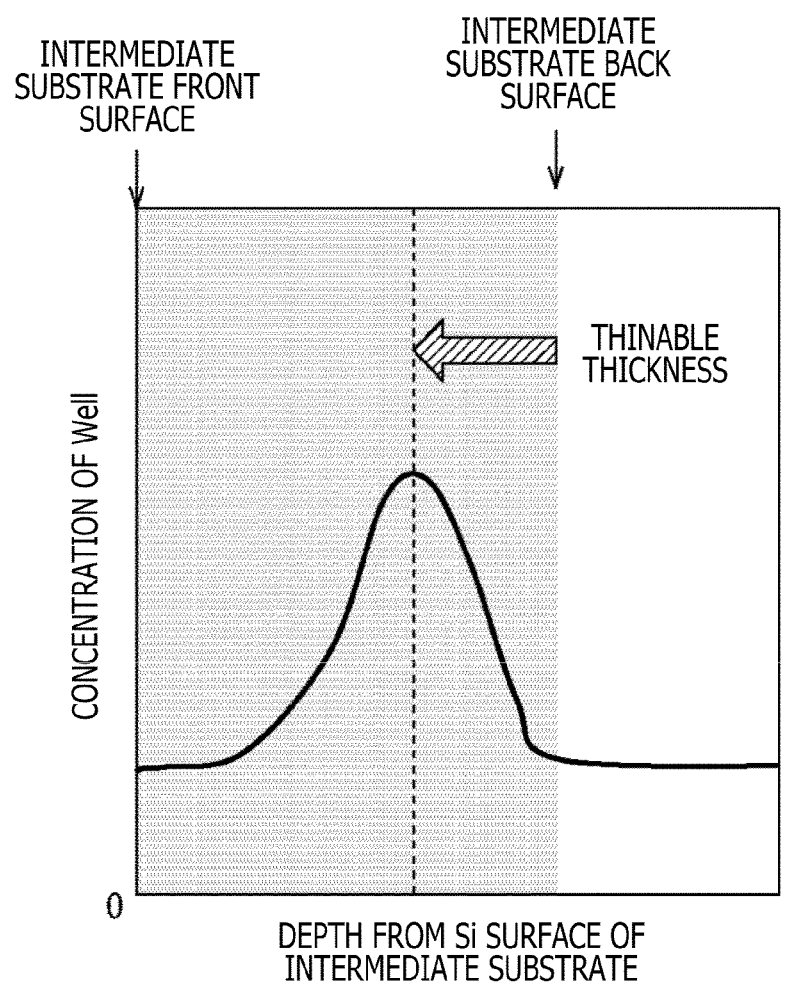
FIG. 6 is a graph depicting a change in concentration of impurities in a well region formed in an intermediate substrate.

FIG. 6 depicts a change in concentration of the impurities in the well region formed in the intermediate substrate 12. As depicted in the figure, the concentration of the impurities in the well region steeply rises from the front surface side to reach a peak, and after reaching the peak, steeply descends. When the intermediate substrate 12 is thinned from the back surface side, the thinable thickness is desirably set up to a thickness which is not beyond the peak of the concentration at most. Consequently, the effectiveness as the constituent element of the semiconductor element can be maintained without impairing the electrical characteristics of the well region.

7. Examples of Application to In-vivo Information Acquisition System

The technology according to the present disclosure (present technology) can be applied to various products. For example, the technology according to the present disclosure may be applied to an endoscope surgery system.

Figure 7:
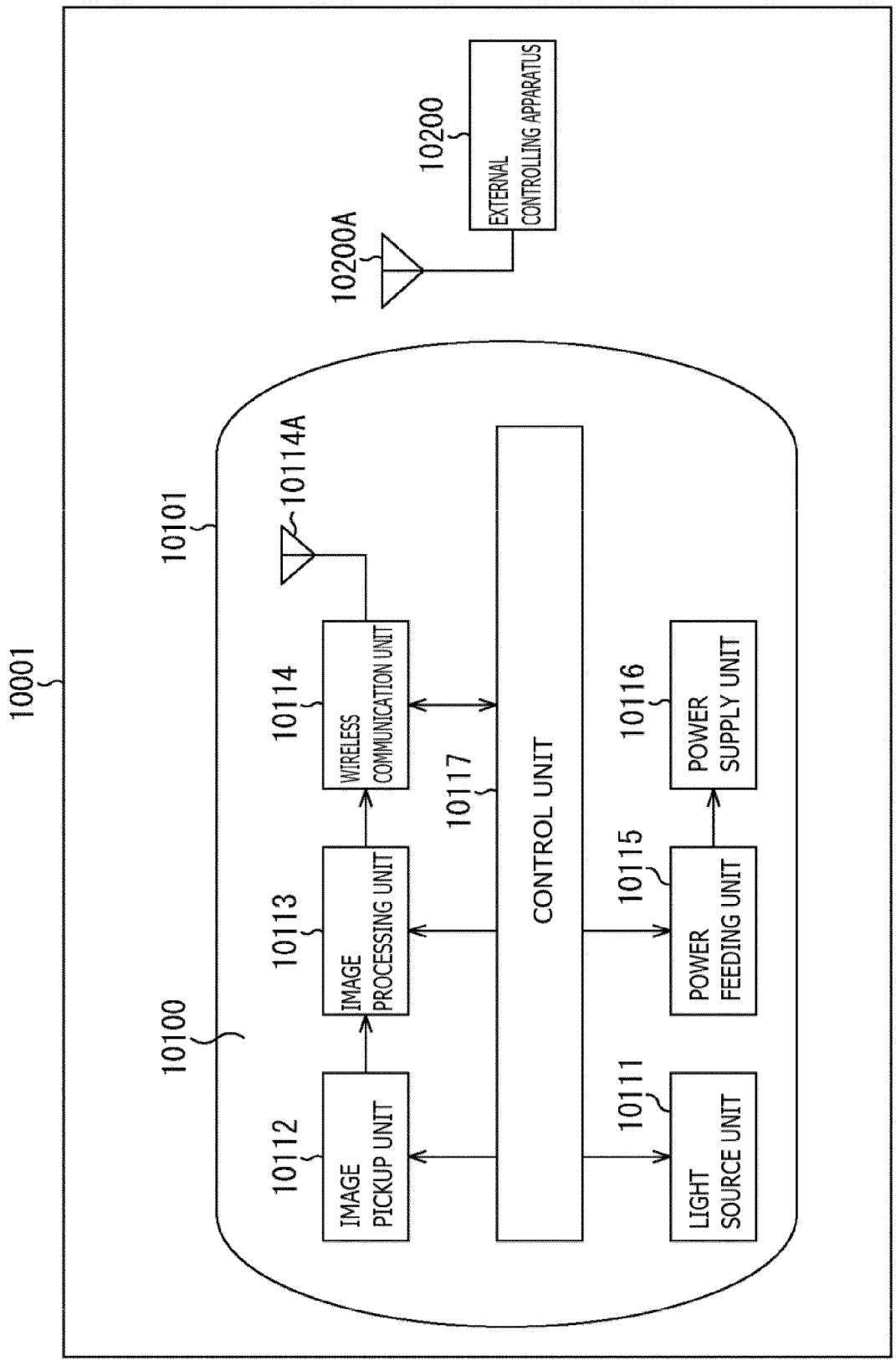
FIG. 7 is a block diagram depicting an example of a schematic configuration of an in-vivo information acquisition system.

FIG. 7 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 7, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

An example of the in-vivo information acquisition system to which the technology according to the present disclosure can be applied has been described so far. The technology according to the present disclosure can, of the configuration described so far, for example, be applied to the image pickup unit 10112.

8. Example of Application to Endoscopic Surgery System

The technology according to the present disclosure (present technology) can be applied to various products. For example, the technology according to the present disclosure may be applied to an endoscopic surgery system.

Figure 8:
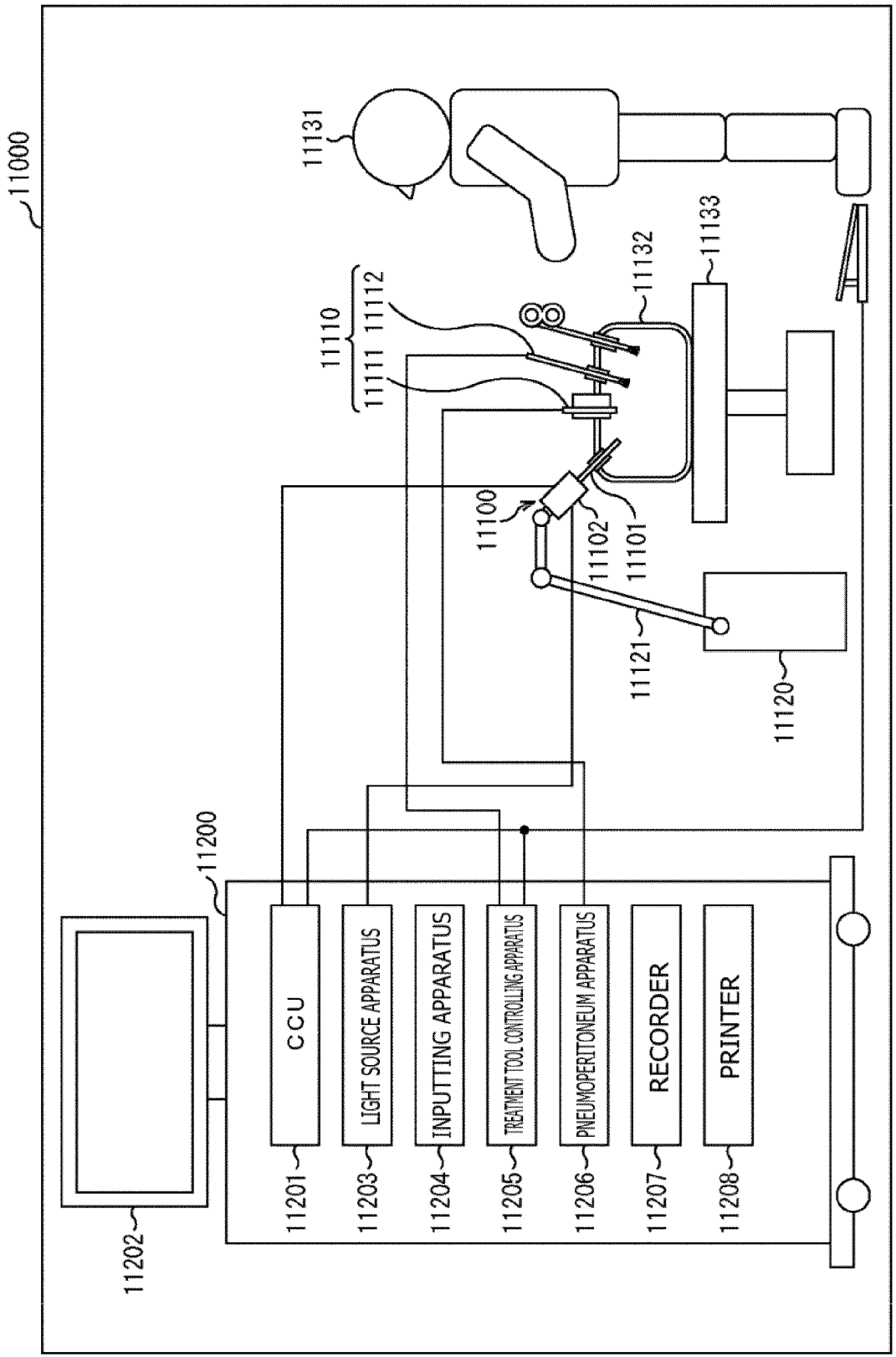
FIG. 8 is a view depicting an example of a schematic configuration of an endoscopic surgery system.

FIG. 8 is a view depicting an example of a schematic configuration of an endoscopic surgery system to which the technology according to an embodiment of the present disclosure (present technology) can be applied.

In FIG. 8, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 9:
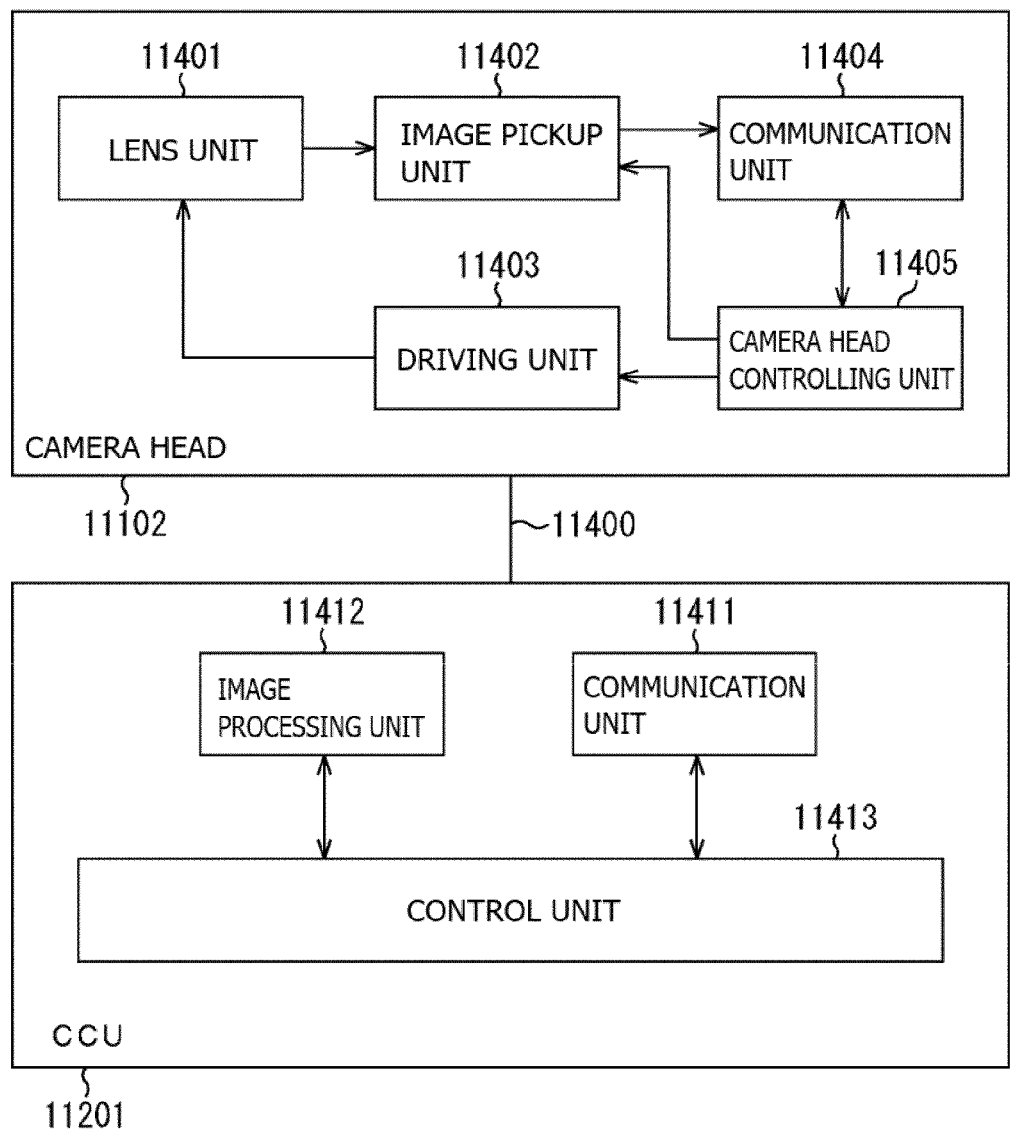
FIG. 9 is a block diagram depicting an example of a functional configuration of a camera head and a camera control unit (CCU).

FIG. 9 is a block diagram depicting an example of a functional configuration of the camera head 11102 and the CCU 11201 depicted in FIG. 8.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

An example of the endoscopic surgery system to which the technology according to the present disclosure can be applied has been described so far. The technology according to the present disclosure can, of the configuration described so far, for example, be applied to the image pickup unit 11402 of the camera head 11102.

It is to be noted that although in this case, the endoscopic surgery system has been described as an example, the technology according to the present disclosure may, for example, also be applied to a microsurgery system or the like in addition thereto.

9. Example of Application to Mobile Body

The technology according to the present disclosure (present technology) can be applied to various products. For example, the technology according to the present disclosure may also be realized as an apparatus mounted to any kind of mobile body such as an automobile, an electric vehicle, a hybrid electric vehicle, a motorcycle, a bicycle, a personal mobility, an airplane, a drone, a ship, or a robot.

Figure 10:
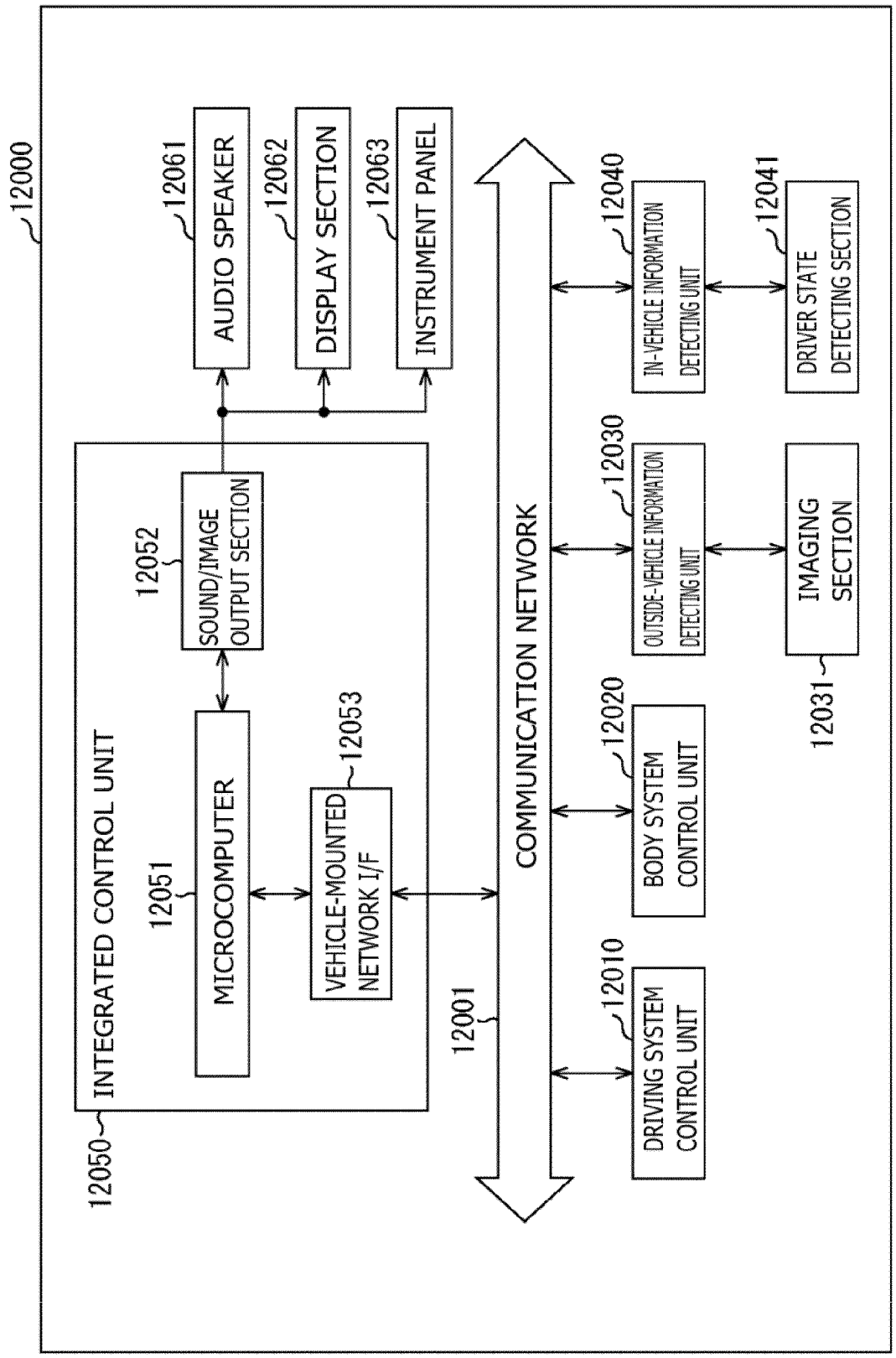
FIG. 10 is a block diagram depicting an example of schematic configuration of a vehicle control system.

FIG. 10 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 10, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 10, an audio speaker 12061, a display section 12062, and an instrument panel 12063 are illustrated as the output device. The display section 12062 may, for example, include at least one of an on-board display and a head-up display.

Figure 11:
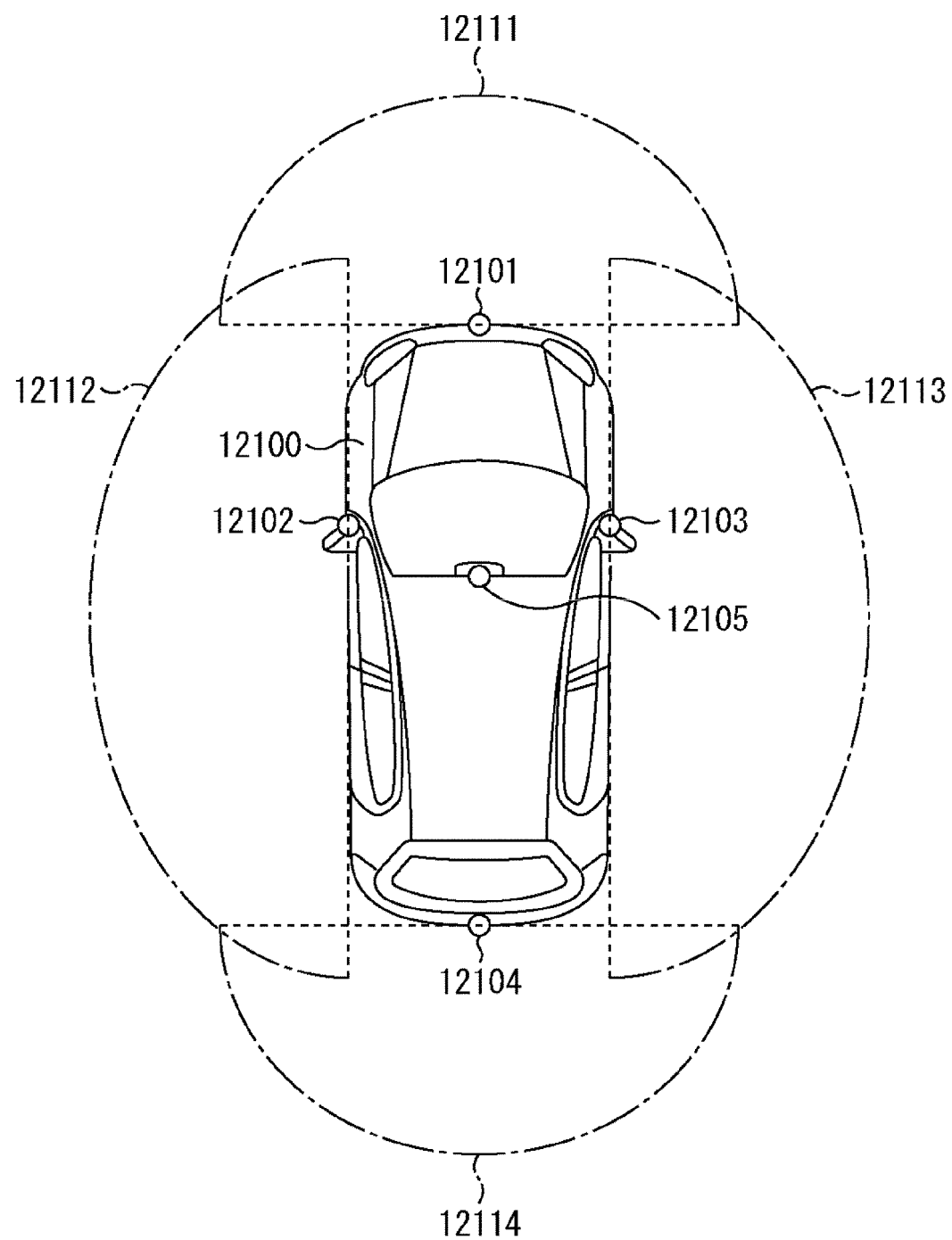
FIG. 11 is a diagram of assistance in explaining an example of installation positions of an outside-vehicle information detecting section and an imaging section.

FIG. 11 is a diagram depicting an example of the installation position of the imaging section 12031.

In FIG. 11, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 11 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

An example of the vehicle control system to which the technology according to the present disclosure can be applied has been described so far. The technology according to the present disclosure may, of the configuration described so far, for example, be applied to the imaging section 12031.

It is to be noted that the embodiment of the present technology is not limited to the embodiments described above, and various changes can be made without departing from the subject matter of the present technology.

The present technology can also adopt the following constitutions.

(1)

A solid-state imaging element constituted by laminating semiconductor substrates in three or more layers, in which of the laminated semiconductor substrate, at least one sheet of the semiconductor substrate is thinned, and an impurity region whose carrier type is the same as that of the semiconductor substrate is formed between a well region and a thinned surface portion in the thinned semiconductor substrate.

(2)

The solid-state imaging element according to (1) described above, in which an impurity region whose carrier type is the same as that of the semiconductor substrate is formed between a well region whose carrier type is different from that of the semiconductor substrate, and the thinned surface portion in the thinned semiconductor substrate.

(3)

The solid-state imaging element according to (1) or (2) described above, in which an impurity region whose carrier type is the same as that of the semiconductor substrate is formed between the well region whose carrier type is different from that of the semiconductor substrate and a well region whose carrier type is the same as that of the semiconductor substrate, and the thinned surface portion in the thinned semiconductor substrate.

(4)

The solid-state imaging element according to any one of (1) to (3) described above, in which a layer including an impurity region whose carrier type is the same as that of the semiconductor substrate is formed over an entire surface between a well region and the thinned surface portion in the thinned semiconductor substrate.

(5)

The solid-state imaging element according to (2) described above, in which the impurity region whose carrier type is the same as that of the semiconductor substrate is formed only between the well region whose carrier type is different from that of the semiconductor substrate and the thinned surface portion in the thinned semiconductor substrate.

(6)

The solid-state imaging element according to any one of (1) to (5) described above, in which in a case where the thinned semiconductor substrate includes a P-type substrate, a P-type impurity region is formed between an Nwell region and the thinned surface portion of the semiconductor substrate.

(7)

The solid-state imaging element according to any one of (1) to (5) described above, in which in a case where the thinned semiconductor substrate includes an N-type substrate, an N-type impurity region is formed between a Pwell region and the thinned surface portion of the semiconductor substrate.

(8)

The solid-state imaging element according to any one of (1) to (7) described above, in which an impurity region whose carrier type is the same as that of the semiconductor substrate is formed at concentration such that it may be impossible for a depletion layer capable of extending from a well region to reach an interface of the semiconductor substrate between the well region and the thinned surface portion in the thinned semiconductor substrate.

(9)

The solid-state imaging element according to any one of (1) to (8) described above, in which a through-via is formed in the thinned semiconductor substrate.

(10)

An electronic apparatus equipped with a solid-state imaging element constituted by laminating semiconductor substrates in three or more layers, in which in the solid-state imaging element, of the laminated semiconductor substrate, at least one sheet of semiconductor substrate is thinned, and an impurity region whose carrier type is the same as that of the semiconductor substrate is formed between a well region and a thinned surface portion in the thinned semiconductor substrate.

(11)

A semiconductor device constituted by laminating semiconductor substrates in three or more layers, in which of the laminated semiconductor substrate, at least one sheet of semiconductor substrate is thinned, and an impurity region whose carrier type is the same as that of the semiconductor substrate is formed between a well region and a thinned surface portion in the thinned semiconductor substrate.

REFERENCE SIGNS LIST

11 Lower layer substrate, 12 Intermediate substrate, 13 Upper layer substrate, 15 Through-via, 21 P-type substrate, 22 Nwell region, 23 Pwell region, 24 P-type region, 31 N-type substrate, 32 N-type region, 44 Connection pad, 51 Resin, 52 Glass substrate

The invention claimed is:

1. A light detecting device constituted by stacking at least three semiconductor sections, comprising:
   a first semiconductor section of the stacked at least three semiconductor sections, wherein the first semiconductor section comprises a pixel region comprising a plurality of photoelectric conversion regions;
   a second semiconductor section, of the stacked at least three semiconductor sections, of a first conductivity type comprising a first well region of the first conductivity type, a second well region of a second conductivity type, an impurity region of the first conductivity type, and a wiring layer; and
   a third semiconductor section bonded with the second semiconductor section,
      wherein the impurity region is disposed between the second well region of the second conductivity type which is different from the first conductivity type, and a bonding surface of the second semiconductor section with one of the first semiconductor section or the third semiconductor section, and
      wherein the impurity region is absent between the first well region of the first conductivity type and the bonding surface of the second semiconductor section with one of the first semiconductor section or the third semiconductor section.

2. The light detecting device according to claim 1, wherein
   the second semiconductor section is a P-type substrate,
   the impurity region is a P-type region, and
   the second well region is an N-type well region.

3. The light detecting device according to claim 1, wherein
   the second semiconductor section is an N-type substrate,
   the impurity region is an N-type region, and
   the second well region is a P-type well region.

4. The light detecting device according to claim 1, wherein a concentration of the impurity region between the second well region and the bonding surface restricts a depletion layer from extending from one of the first well region or the second well region to reach an interface of the second semiconductor section between both the first well region and the second well region and the bonding surface of the second semiconductor section.

5. The light detecting device according to claim 1, wherein a through-via is formed in the second semiconductor section.

6. An electronic apparatus equipped with a light detecting device constituted by stacking at least three semiconductor sections,
wherein the light detecting device comprises:
a first semiconductor section of the stacked at least three semiconductor sections, wherein the first semiconductor section comprises a pixel region comprising a plurality of photoelectric conversion regions;
a second semiconductor section, of the stacked at least three semiconductor sections, of a first conductivity type comprising a first well region of the first conductivity type, a second well region of a second conductivity type, an impurity region of the first conductivity type, and a wiring layer; and
a third semiconductor section bonded with the second semiconductor section,
wherein the impurity region is disposed between the second well region of the second conductivity type which is different from the first conductivity type, and a bonding surface of the second semiconductor section with one of the first semiconductor section or the third semiconductor section, and
wherein the impurity region is absent between the first well region of the first conductivity type and the bonding surface of the second semiconductor section with one of the first semiconductor section or the third semiconductor section.

7. A semiconductor device constituted by stacking at least three semiconductor sections, comprising:
a first semiconductor section of the stacked at least three semiconductor sections, wherein the first semiconductor section comprises a pixel region comprising a plurality of photoelectric conversion regions;
a second semiconductor section, of the stacked at least three semiconductor sections, of a first conductivity type comprising a first well region of the first conductivity type, a second well region of a second conductivity type, an impurity region of the first conductivity type, and a wiring layer; and
a third semiconductor section bonded with the second semiconductor section,
wherein the impurity region is disposed between the second well region of the second conductivity type which is different from the first conductivity type, and a bonding surface of the second semiconductor section with one of the first semiconductor section or the third semiconductor section, and
wherein the impurity region is absent between the first well region of the first conductivity type and the bonding surface of the second semiconductor section with one of the first semiconductor section or the third semiconductor section.

* * * * *